United States Patent

Aizu et al.

[11] Patent Number: 5,074,307
[45] Date of Patent: Dec. 24, 1991

[54] OPHTHALMOLOGICAL DIAGNOSIS APPARATUS

[75] Inventors: Yoshihisa Aizu, Machida; Kohji Ogino, Hino, both of Japan

[73] Assignee: Kowa Company Ltd., Japan

[21] Appl. No.: 488,713

[22] Filed: Mar. 5, 1990

[30] Foreign Application Priority Data

Mar. 6, 1989 [JP] Japan ................................ 1-51953
Mar. 6, 1989 [JP] Japan ................................ 1-51954

[51] Int. Cl.⁵ .......................................... A61B 3/10
[52] U.S. Cl. .................................. 128/666; 128/691;
356/28.5; 351/206; 351/211; 351/221
[58] Field of Search .................. 128/691, 666; 606/4;
351/205, 206, 211, 213, 214, 221; 356/28, 28.5

[56] References Cited

U.S. PATENT DOCUMENTS

| 4,402,601 | 9/1983 | Riva | 128/666 X |
| 4,743,107 | 5/1988 | Aizu et al. | 128/691 X |
| 4,979,818 | 12/1990 | Kobayashi | 128/691 X |

*Primary Examiner*—Ruth S. Smith
*Attorney, Agent, or Firm*—Bruce L. Adams; Van C. Wilks

[57] ABSTRACT

An ophthalmological diagnosis apparatus is provided in which a laser beam is projected at a region of the eye fundus to produce a laser speckle pattern formed by light scattered from tissues of the eye fundus. Movement of the speckle pattern is detected to produce a speckle signal which is photon-counted as photoelectric pulses per unit sampling time. A rate of fluctuation of correlation function data is evaluated, on the basis of which the radius of the detecting aperture is determined. This makes it possible to sample accurate data with good reproducibility.

7 Claims, 5 Drawing Sheets

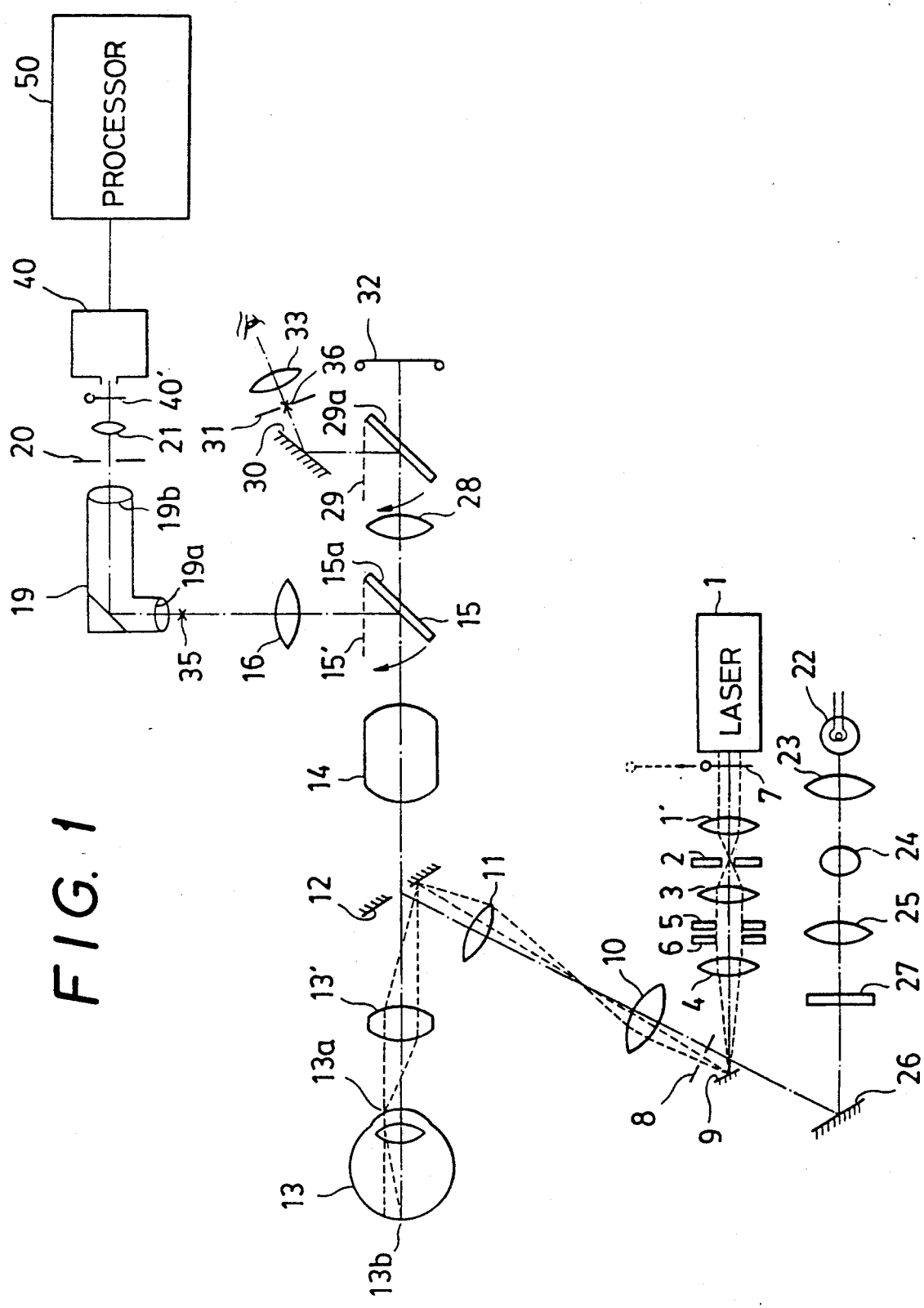

OPHTHALMOLOGICAL DIAGNOSIS APPARATUS

BACKGROUND OF THE INVENTION

1. Field of the Invention

This invention relates to an ophthalmological diagnosis apparatus, particularly to an ophthalmological diagnosis apparatus in which a laser beam of prescribed diameter is projected at a region of the eye fundus to produce a laser speckle pattern formed by light scattered from tissues of the eye fundus, and movement of the laser speckle pattern is photoelectrically detected through a minute circular detecting aperture as fluctuation in the light intensity of speckles at an observation plane, thereby producing a speckle signal whose photon correlation function is calculated to determine the blood flow state in the eye fundus tissue.

2. Description of the Prior Art

Conventional laser Doppler methods of measuring blood flow in retinal and other tissue by illuminating the eye fundus with a laser beam include those described in "Investigative Ophthalmology," vol. 11 No. 11, p 936 (November 1972) and "Science," vol. 186 (November 1974) p 830, and in Japanese Unexamined Patent Publication Nos. 55-75668, 55-75669, 55-75670, 52-142885 (corresponding to GB 13132/76 and U.S. Pat. No. 4,166,695), 56-125033 (corresponding to GB 79/37799), 58-118730 (corresponding to U.S. Pat. No. 4,402,601) and U.S. Pat. No. 4,142,796. However, these laser Doppler methods involve the use of a high precision optical system, are complicated to use and provide results which lack repeatability and reliability, which hinder the practical utilization of the method.

In order to overcome the aforementioned drawbacks the present inventors have adapted laser speckle methods used for blood flow measurement in skin and the like (such as the methods described in Japanese Unexamined Patent Publication Nos. 60-199430, 60-203235 and 60-203236 and in "Optics Letters," vol. 10 No. 3 (March 1985) p 104) for ophthalmological applications involving evaluating the state of the blood flow in tissues of the eye fundus, and have filed the following related patent applications: Japanese Unexamined Patent Publication Nos. 62-275431 (U.S. Pat. No. 4,743,107 and EPC 234869), 63-238843 (EPC 284248) and 63-242220 (EPC 285314).

In the methods described in these publications with respect to eye fundus measurements, a detecting aperture is used to extract time-base fluctuations in the intensity of speckles formed at an optical Fourier Transform plane with respect to the eye fundus, or at the Fraunhofer refraction plane, or at an image plane (or a magnified image plane) that is conjugate with respect to the eye fundus.

If the large diameter of the detecting aperture is too large in comparison with the averaged diameter of the speckles at the detection plane, the averaging of the speckles (also called integration effect) by which the intensity fluctuation thereof at the detecting aperture is canceled. This causes the detected speckle signal to have a reduced contrast and a degraded S/N ratio.

If the diameter of the detecting aperture is smaller than the averaged diameter of the speckles, on the other hand, the signal has a very low intensity, thus making measurement itself difficult. The criterion is, therefore, such that the aperture diameter should be selected so as not to be too large or small in comparison with the averaged speckle diameter or the aperture diameter should be set so as to be substantially equal thereto. Because no decision is made based on definite criterion, the conditions relative to the detected light quantity or signal contrast are not constant and an optimum condition is not obtained.

On the other hand, a point-like detecting aperture is recommended for speckle velocimetry so as to enable precise reproduction of the speckle intensity fluctuation, as is disclosed in "The Review of Laser Engineering" (The Laser Society of Japan) Vol. 8, No.2 (1980, March) p.37 and No. 3(1980, May) p.3 or "Applied Physics" (Springer-erlag) Vol. 25(1981) p. 179. In fact, a definite aperture must be used to obtain a certain amount of light. No suggestion is, however, made as to how an optimum detecting aperture should be set.

Since the intensity of the speckle pattern obtained by light scattered from the eye fundus is very low, the photon correlation method is required for measurement. This method is, however, not effective when an optimum condition is not set to take into account the light quantity and signal contrast.

With respect to the shape of the detection aperture, proposal was made of a rectangular aperture, which, however, didn't provide advantages because, instead of translational motion, boiling motion of random blinking speckles dominates at the detection plane even if blood cells flow in a predetermined direction in the blood vessel. It has thus been found that a circular detection aperture is preferable for random motion.

On the other hand, the photon correlation function is impractical when the measured data have no sufficient light quantity and contrast because no convergence of correlation data is expected. The measured data of poor convergence were evaluated by visual observation, which was, however, ambiguous and subjective. Thus, there was a problem that the same data were employed or not employed because they visually converge or don't.

SUMMARY OF THE INVENTION

It is, therefore, an object of the invention to provide an ophthalmological diagnosis apparatus which is capable of providing objective measurement data.

According to the invention, a laser beam of prescribed diameter is projected at a region of the eye fundus to produce a laser speckle pattern formed by light scattered from tissues of the eye fundus, and movement of the laser speckle pattern is photoelectrically detected through a minute circular detecting aperture as fluctuation in the light intensity of speckles at an observation plane, thereby producing a speckle signal whose photon correlation function is calculated to determine the blood flow state in the eye fundus tissue. In such an arrangement, means are provided for evaluating a rate of fluctuation of correlation function data, on the basis of which the radius of the detecting aperture is determined.

In the apparatus in the invention, the convergence of the photon correlation function is evaluated quantitatively to provide a condition for the detecting aperture, thus making it possible to produce accurate correlation data having a small fluctuation rate. The aperture radius is preferably set to be one to five times as great as the averaged diameter of speckles to be detected. The employment of the measured data is made dependent on a comparison of the convergence with a reference value, thus making it possible to sample accurate data with good reproducibility.

BRIEF DESCRIPTION OF THE DRAWINGS

The objects and features of the present invention will become more apparent from a consideration of the following detailed description taken in conjunction with the accompanying drawings in which:

FIG. 1 is a schematic diagram of the arrangement of an embodiment of an apparatus employing the method of the invention;

DETAILED DESCRIPTION OF THE PREFERRED EMBODIMENTS

Figure 3:
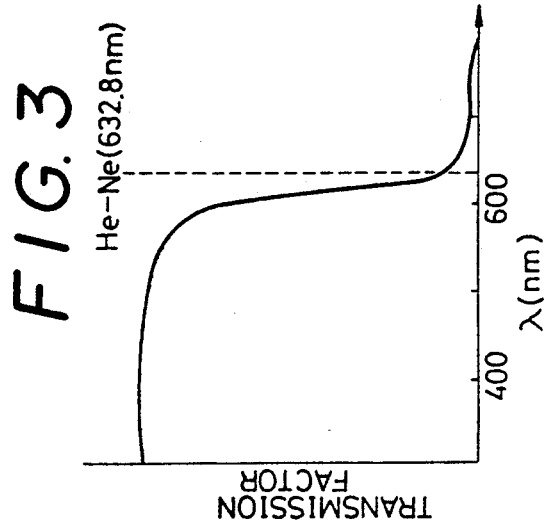
FIG. 3 is a characteristic curve showing the characteristics of a wavelength separation filter used in the embodiment of FIG. 1.

The invention will now be described in detail with reference to the embodiment shown in the drawings. The invention is concerned specifically with the fundus region of the eye, and as such the following description relates to when an eye fundus camera is used to measure blood flow in the eye fundus.

FIG. 1 shows an overall schematic view of an apparatus for carrying out the measurement method according to the present invention. A laser beam such as from a red-light He-Ne (wavelength: 632.8 nm) type laser beam source 1, for example, passes through a condenser lens 1' and a light quantity adjustment filter 2 for adjusting the intensity of the beam. The beam then passes through relay lenses 3 and 4 and enters the eye fundus illuminating projector of an eye fundus camera.

Figure 2:
FIG. 2 is a diagram showing the structure of a ring slit.

Two stops 5 and 6 are disposed between the relay lenses 3 and 4 for selectively adjusting the size and shape of the region of the eye fundus irradiated by the laser beam. Disposed near the beam-emitting end of the laser beam source 1 is a shutter 7 which can be opened or closed as required. As shown in FIG. 2, the laser beam issuing from the relay lens 4 is reflected by a mirror 9 provided in one portion of an annular aperture 8a formed in a ring slit 8 disposed in the eye fundus illuminating projector, so that the reflected laser beam travels along the same light path to the eye fundus as that followed by the beam of light directed into the eye fundus to provide illumination for photography and observation. As a result, the laser beam passes through relay lenses 10 and 11, is reflected by a ring mirror 12, is converged on the cornea 13a of the eye under examination 13 by an objective lens 13' and then diverges at the eye fundus 13b to thereby form a projected region which is larger than the diameter of the blood vessel of interest.

This area is also illuminated by the illuminating projector of the fundus camera, facilitating observation. The system which provides the illumination for observation is constituted of an observation light source 22, a condenser lens 23, a condenser lens 25, a filter 27 and a mirror 26 disposed on the same light path as a photographic light source 24. As the path of the laser beam coincides with that of the beam of photographic and observation light, the laser beam can be made to impinge on the desired region of the eye fundus 13b by mechanisms for swinging and tilting the eye fundus camera vertically and horizontally and also by use of the eye fixation means.

The filter 27 disposed between the condenser lens 25 and the mirror 26 is a wavelength separation filter with the characteristics shown in FIG. 3, thereby filtering out red components from the observation and photographic light.

Speckle light produced by the scattering of the laser beam from blood cells moving in the blood vessels in the eye fundus enters the objective lens 13', passes through the ring mirror 12 and then through a photographic lens 14 to impinge on a wavelength separation mirror 15. Like the filter 27, the wavelength separation mirror 15 exhibits the type of spectral characteristics illustrated in FIG. 3, and since it therefore reflects most of the red light components and transmits other light, it reflects most of the speckle light (red) generated by the He-Ne laser beam. A lens 16 forms the reflected light into an image at an image plane 35 and is then magnified by an objective lens 19a and eyepiece lens 19b of a microscope optical system 19. The magnified image passes through a detecting aperture 20, is converged once again by a condenser lens 21 and detected by a photomultiplier 40. A shutter 40' is disposed in front of the photomultiplier 40 and the output signal obtained from the photomultiplier 40 when this shutter is open is input to a signal processor 50.

Figure 4:
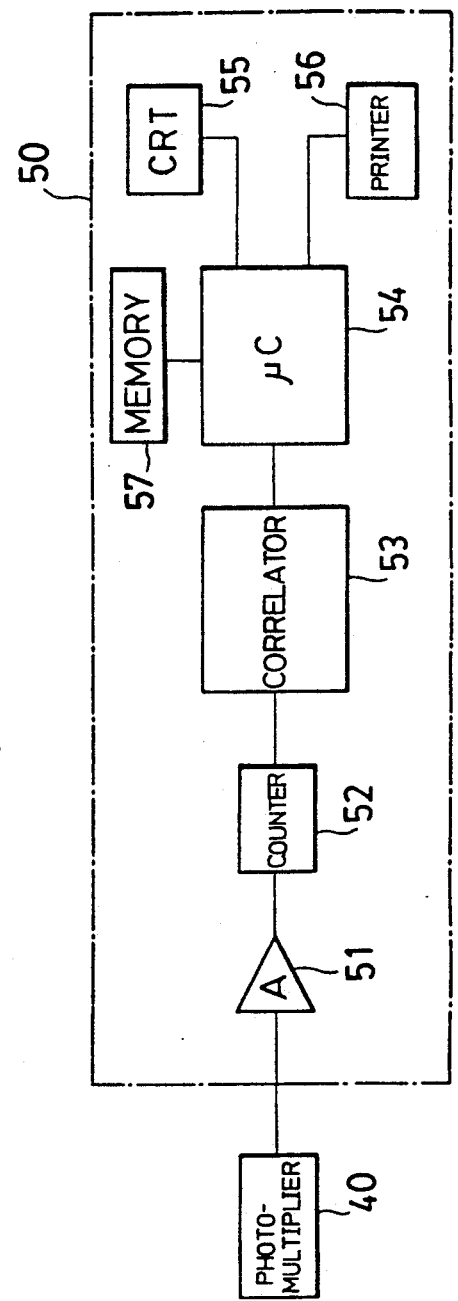
FIG. 4 is a block diagram showing the arrangement of a signal processor used in the embodiment of FIG. 1.

As shown in FIG. 4, the signal processor 50 is constituted of an amplifier 51, photon counting unit 52, a correlator 53, a microcomputer 54, a CRT display 55, a printer 56 and a memory 57.

The light passing through the wavelength separation mirror 15 advances through a relay lens 28, is reflected by a swingable mirror 29 and a mirror 30, and is then directed, via a reticle 31, to an eyepiece 33 through which it can be observed or recorded on a photographic film 32.

With the apparatus arranged as described, after the power has been turned on and the patient positioned, the eye fundus 13b of the eye 13 under examination is observed by means of the observation light optical system constituted by the elements 22 to 26. The laser light beam source 1 is then activated. At this point the filter 2 is used to adjust the light output to the level used for system set-up and the stops 5 and 6 are used to set the size and shape of the region illuminated by the laser beam. Next, the shutter 7 is opened and, after the measurement position has been set, the speckle pattern is confirmed by means of the observation light optical system constituted by the elements 28 to 31.

With respect to this embodiment, to facilitate the laser beam projection, the size of the region of the eye fundus 13b projected by the laser beam at the portions at which measurement is to be carried out is made larger in diameter than the blood vessel, such as a diameter of 1 mm to 3 mm. This may therefore result in the inclusion of a plurality of relatively thick blood vessels in addition to capillaries. If the detection is made at the Fourier plane relative to the eye fundus, the rays of light scattered from all the illuminated regions are superimposed with the result that the analysis based on the speckles indicates an overall evaluation of a state of blood flow for all the blood vessels included in the illuminated region. It is thus recommendable to detect the speckle pattern at a magnified image plane as shown in FIG. 1 if the blood flow of a specific blood vessel is to be measured.

It is, however, needless to say that the invention is applicable to detection at both of the Fourier transform plane (Fraunhofer refraction plane) and image plane (magnified image plane). The following description will be made with reference to the detection at the image plane.

To measure the blood flow in a specific blood vessel, the blood vessel to be measured is selected at the magnified image plane and the detecting aperture 20 is then located within the blood vessel image at the magnified image plane. Thus, a conjugate image of the eye fundus is formed at the image plane 35 shown in FIG. 1 and the image is then magnified by the objective lens 19a and eyepiece lens 19b of the microscope optical system 19, and fluctuations in the intensity of the speckle light are detected by the detecting aperture 20 disposed at the magnified image plane. The light is then converged by a condenser lens 21 and converted into an electrical signal by the photomultiplier 40, the shutter 40' being in the open position.

The output produced by the photomultiplier 40 during measurement constitutes a speckle signal which varies with time in accordance with the movement of the blood cells. This speckle signal is amplified by the amplifier 51 in the signal processor 50, and by means of the photon counting unit 52, time series data of the photoelectric pulses corresponding to the intensity of the light are produced. The correlator 53 produces a photon correlation function, which is analyzed for evaluation by the microcomputer 54 for display on the CRT 55 or printer 56.

As thus described in the foregoing, since in accordance with this embodiment the detecting aperture 20 is disposed at the magnified image plane, the blood flow in a specific single blood vessel can be measured by selecting the blood vessel in the region by the laser beam and locating the detecting aperture 20 within the blood vessel image, either by adjusting the position of the detecting aperture 20 or by adjusting the fixation of the eye under examination 13.

Figure 5:
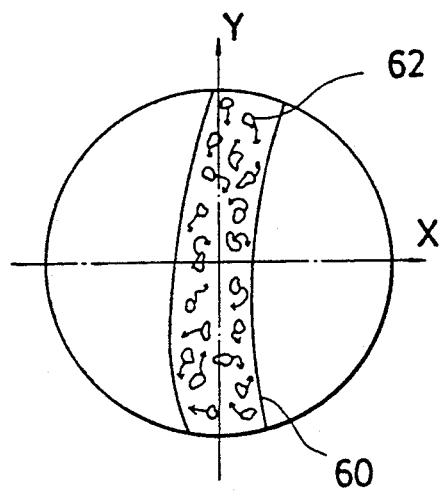
FIG. 5 is a diagram showing image plane speckles observed at the detecting aperture plane.
Figure 6:
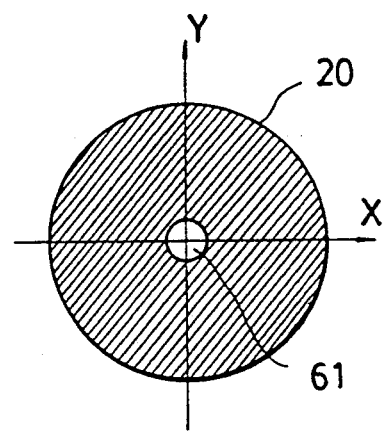
FIG. 6 is a diagram of a detecting aperture.

The detecting aperture 20 may be a pinhole. A magnified image of a desired single blood vessel 60 such as that shown in FIG. 5 can be observed. If a pinhole such as the pinhole 61 shown in FIG. 6 having a smaller diameter than that of the observed blood vessel image is disposed at a portion where the image plane speckles within the blood vessel are in motion, speckles passing across the detecting aperture 20 will give rise to a corresponding fluctuation in the intensity of the detected light, thereby producing a speckle signal.

It is observed that speckles 62 produced by in vivo tissue exhibit a characteristic boiling motion caused by multiple scattering. Unlike translational motion, which is observed when image plane speckles 62 move in one direction without any change, boiling motion refers to what appears as a random, flickering motion of the image plane speckles 62, which ceaselessly change in intensity. It is, however, needless to say that speckle signals can also be derived from such speckles exhibiting fluctuation in intensity at the pinhole 61.

Figure 7:
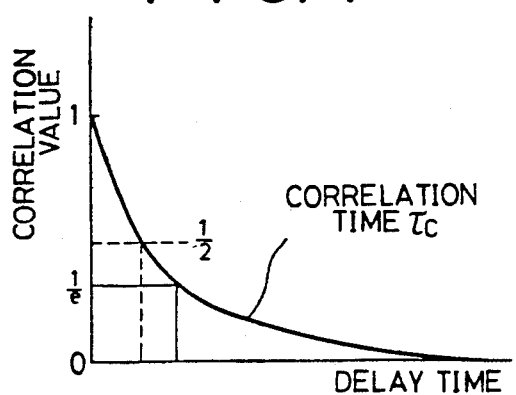
FIG. 7 is a graph showing the relationship between time delay and correlation value.
Figure 8:
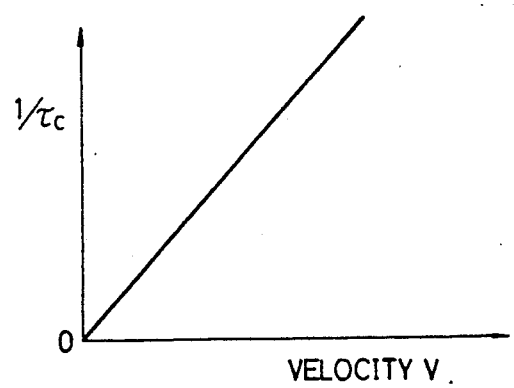
FIG. 8 is a graph showing the relationship between velocity and correlation value.

As the rate at which image speckles 62 fluctuate changes in proportion to the velocity of the blood flow, an increase in the velocity of the blood flow produces a corresponding increase in the rate at which the speckle signal varies with time, which increases the high frequency component of the signal. After the autocorrelation function of the signal is obtained with the signal processor 50, the degree of attenuation is evaluated in accordance with the correlation time. If, as shown in FIG. 7, correlation time $\tau c$ is taken as the time delay for the correlation value to become $1/e$ (or $\frac{1}{2}$ or the like), the relationship between the inverse thereof $1/\tau c$ and image plane speckle velocity will be linear. As the fluctuation velocity of the image plane speckles 62 directly reflects blood flow velocity, blood flow velocity V can be evaluated from $1/\tau c$ from the relationship shown in FIG. 8.

There is a necessity of projecting a laser beam as weak as possible in a short time for safety reasons. A measurement in a short time is further necessary in view of the fact that influences due to eye movement during measurement or oscillation of the total measuring system must be avoided or that the patient's burden must be reduced. The eye fundus, however, has a low reflection index, so that the best method is to improve the sensitivity to detect the light quantity on the detection side.

Figure 9:
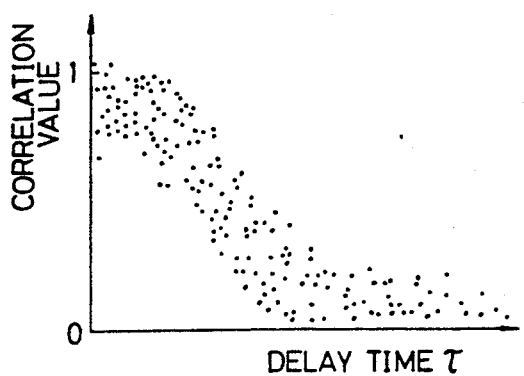
FIGS. 9 to 11 are graphs each showing measured correlation data.
Figure 10:
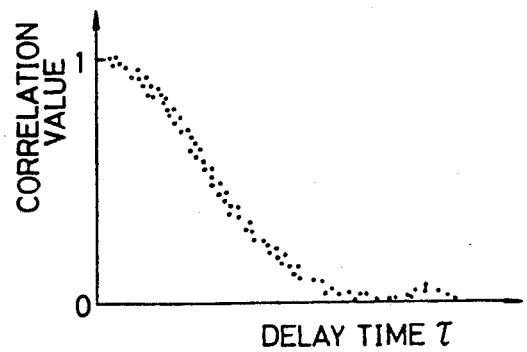
Figure 11:
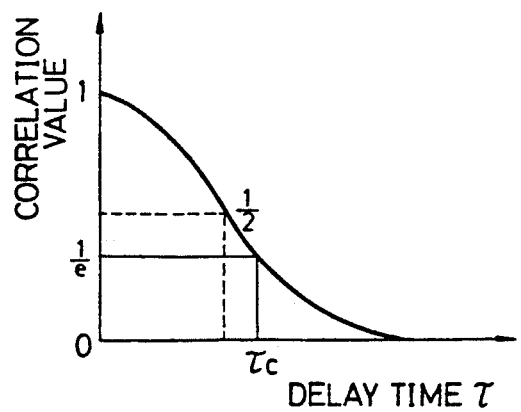

Under such circumstances, the invention is intended to provide detection conditions for obtaining optimum measurement results. The measured data are, as shown in FIGS. 9 and 10, plotted and displayed as a correlation function. The computer smooths the correlation function, as shown in FIG. 11. Insufficient integration (convergence) of the data due to fluctuation as shown in FIG. 9 produces a big error and makes it impossible to determine the correlation time $\tau c$. The big fluctuation degrades the smoothing accuracy and the evaluation of the correlation time $\tau c$.

To obtain data with sufficient convergence, the convergence of the data is evaluated quantitatively on the basis of a fluctuation rate of the data. It will be more fully described in the following how to define the fluctuation rate.

Figure 12A:
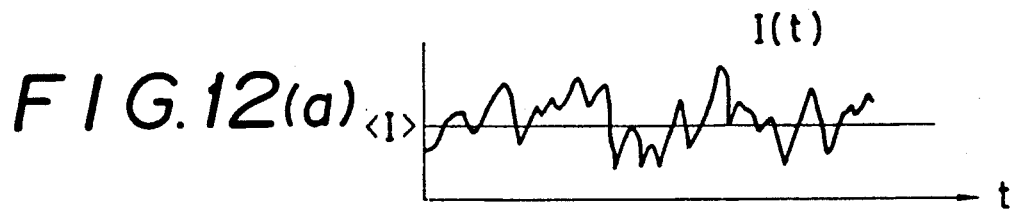
FIGS. 12a to 12c show signal waves each illustrating the correlation calculation for an input signal.
Figure 12B:
Figure 12C:
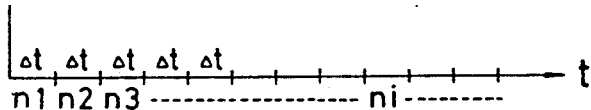

The signal from the photomultiplier 40 indicates a speckle signal which, for example, varies with time as blood cells move in the eye fundus, as is shown by a symbol $I(t)$ in FIG. 12a. The mean $<I>$ corresponds to a DC component which is obtained when the signal $I(t)$ is averaged over the measuring time. The signal $I(t)$ is then amplified by the amplifier 51 in FIG. 4, and photoncounted by the photon counting unit 52, which produces a train of pulses the number of which is proportional to the intensity of the signal. The pulses appear as shown in FIG. 12b and their density per unit time becomes greater as the light intensity becomes great. The number of the pulses are counted in the digital correlator 53 for every predetermined sampling interval $\Delta t$ to derive therefrom counted values $n1, n2, n3, \ldots ni$. Based on these counted values, the digital correlator 53 calculates an autocorrelation function, $$g(C\Delta\tau) = \sum_{i=1}^{N} n_i^* n_{i+c} \quad (1)$$

where it is assumed that the delay time is equal to the sampling interval.

Figure 13:
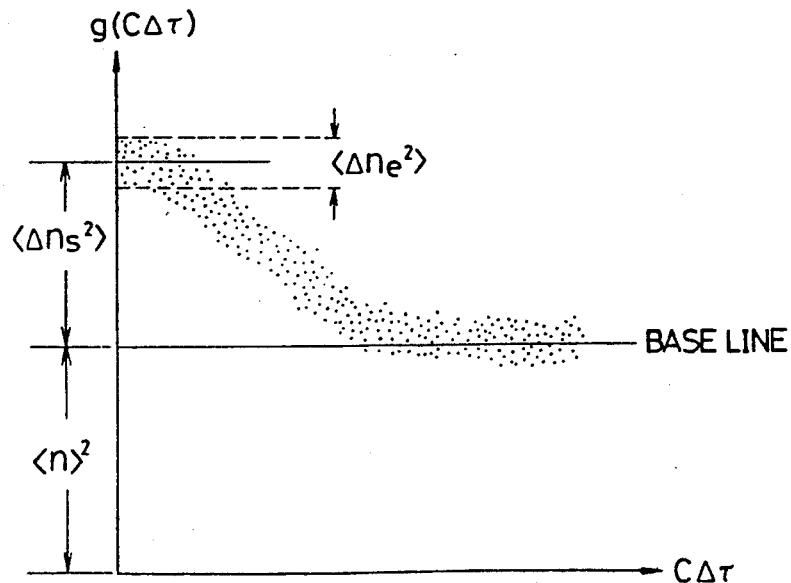
FIGS. 13 and 14 are views each illustrating a fluctuation in correlation function.

The plotted data are shown as an autocorrelation function curve in FIG. 13. It will be understood that insufficiently integrated data cause non-convergence of data, thus fluctuating within a certain range. The value of the formula (1) increases with the increasing measuring time and increasing number N of the sampling data. The level of the base line is expressed by $<n>^2$, where $<n>$ is the average of the total number of data per measuring time T, i.e. the averaged number of pulses per sampling interval $\Delta t$. The level above the base line is indicated by $<\Delta ns^2>$.

The $<\Delta ns^2>$ refers to a variance of fluctuation component $\Delta nsi = nsi - <n>$. The effective width of spread over which the data fluctuate can be given by $<\Delta ne^2>$. The $<\Delta ne^2>$ shows that the photon-counted value fluctuates around the mean $<ne>$ by a certain amount even if a constant intensity of light is successfully detected. This thus indicates the variance of fluctuation due to photo counting.

Figure 14:
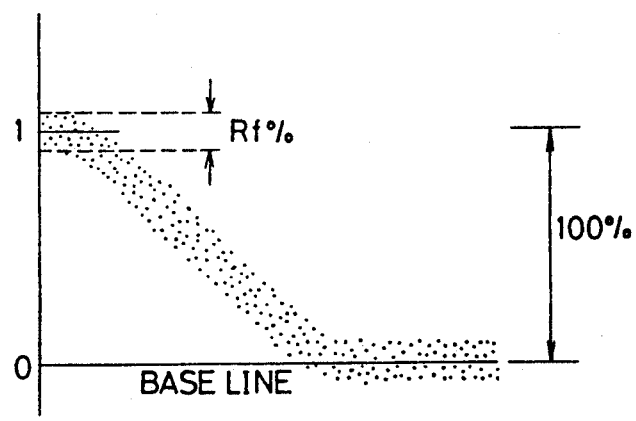

Usually, the base line is subtracted from the correlation curve, as shown in FIG. 14, and the upper portion thereof is referred to as a correlation curve. To determine the convergence of correlation data quantitatively, it is preferable to determine a ratio of fluctuation width $<\Delta ne^2>$ of data to the level of the correlation curve $<\Delta ns^2>$. Thus, a rate of fluctuation Rf is defined by $$RF = (<\Delta ne^2>/<\Delta ns^2>)*100\% \quad (2)$$

If the probability distribution for photon-counted fluctuation follows a Poisson process, the numerator $<\Delta ne^2>$ in the formula (2) can be expressed as $$<\Delta ne^2> = \sqrt{ms} <n> \quad (3)$$

On the other hand, the denominator $<\Delta ns^2>$ is $$<\Delta ns^2> = ms \, Cs <n>^2 \quad (4)$$

where Cs is the square of the contrast of input signal
$$C = \sqrt{<\Delta I^2>}/<I>$$

and thus equal to a ratio of $<\Delta ns^2>/<n>^2$ in FIG. 14. Also, note that $\Delta I = I(t) - <I>$.

Thus, the rate of fluctuation Rf is given by the above formulas as follows:

$$Rf = 100/(Cs<n> \sqrt{T/\Delta t}) \, (\%) \quad (5)$$

It will be appreciated that the expression (5) makes it possible to evaluate the convergence of the plotted correlation function curve. Rf (%) refers directly to a rate of fluctuation width in terms of percent with the level of the curve being 100%. This is very practical and effective because the result of the visual observation can be expressed quantitatively.

The correlation data whose rate of fluctuation are substantially equal to each other can be thus compared under the same error conditions. This is very preferable in the case of obtaining the correlation time $\tau c$ corresponding to a delay time at which the correlation value falls from 1 to 1/e, or in the case of analyzing the shape or configuration of the correlation curve. It can previously be determined, for example, that data with their rate of fluctuation under 10% are employed and others not employed. The microcomputer 54 then performs the calculation for the measured correlation data according to the formula (5) and outputs the rate of fluctuation on the spot. This enables the recording or analysis of only the data that are necessary not on the basis of a visual observation, but according to a predetermined criterion, thus improving the quality of data sampled.

The formula (5) further shows that the rate of fluctuation for evaluating the convergence of the correlation function is dependent upon the measuring time T, sampling interval $\Delta t$, averaged number $<n>$ of photon-counted pulses per one sampling interval $\Delta t$ and factor Cs which represents the square of the contrast of the input signal. Thus, if these parameters or measuring conditions are given, it is possible to evaluate the rate of fluctuation Rf prior to measurement. The formula (5) further indicates how the parameters must be adjusted in order to obtain a desired value of Rf. For example, the formula (5) teaches that twice the intensity also makes twice $<n>$ with the result that the rate of fluctuation Rf is reduced to a half with twice the improvement in convergence. On the other hand, it will be understood that it is necessary to make the measuring time T four times longer in order to obtain half the rate of fluctuation Rf.

Thus, the apparatus according to the invention provides quantitative evaluation for convergence of the correlation function when the photon correlation is used for dynamic light scattering. The convergence evaluation according to the formula (5) is particularly suitable for a very low intensity of light because the correlation curve is not expected to converge under such circumstances.

Suppose, for example, that the ophthalmic measurement apparatus in FIG. 1 is used to detect the fluctuation of the speckle pattern obtained by illuminating the eye fundus with a beam of laser light and to derive therefrom a photon correlation curve in order to obtain medical information such as blood flow in the eye fundus. For parameters such as the amount of laser illumination or measuring time there are provided some restrictions in view of safety. The examiner cannot further adjust the contrast of the speckle pattern from the eye fundus because it is closely associated with the living tissue to be measured. Under such circumstances, it would be very preferable to be able to evaluate quantitatively how the correlation curve converges. This is because it can be analyzed easily how the parameters such as the intensity of detection light, signal contrast, measuring time, and sampling interval should be set to provide good results. It is apparent that much light can be detected if the detection aperture is made greater in diameter than the average diameter of the speckles, but this disadvantageously causes reduction in the signal contrast. Such adjustment, however, can be successfully evaluated by finding the minimum fluctuation rate Rf to determine the optimum diameter of the detection aperture using the formula (5).

Next, how the optimum detecting aperture is determined will be described.

The variables in the above formula (5) are to be studied to make the fluctuation rate Rf as small as possible and improve the convergence of the data. The variables Cs and $<n>$ are remarkably dependent on the diameter of the minute circular detecting aperture in use, which is thus determined so as to make the fluctuation rate as small as possible.

Figure 15:
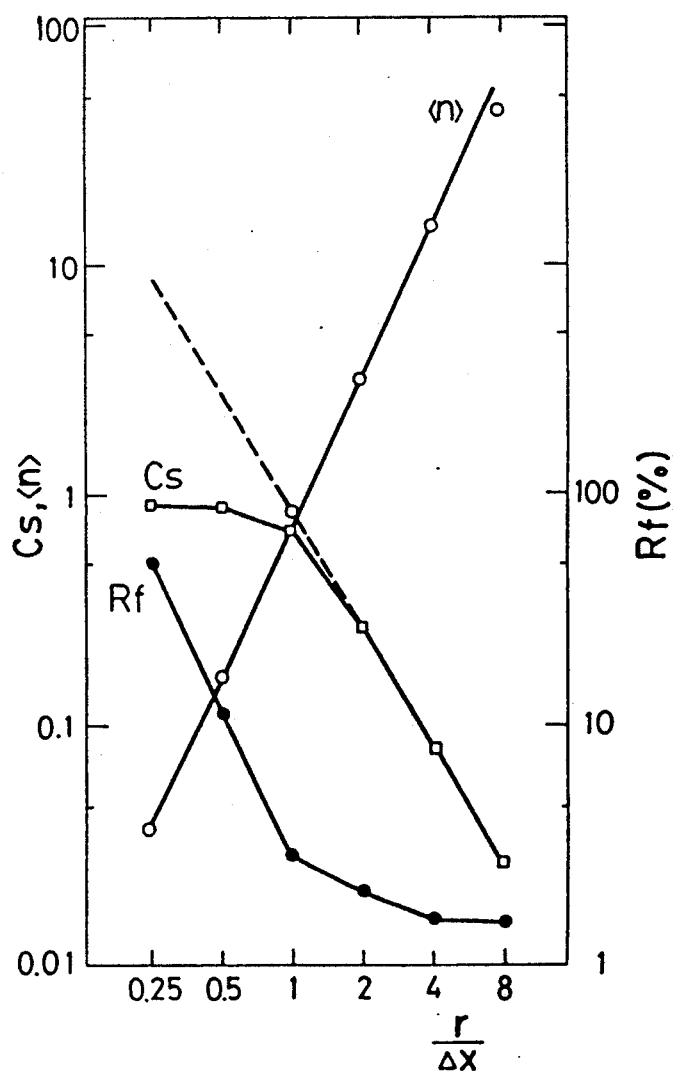
FIG. 15 is a graph showing transitions of the parameters when the aperture diameter is changed.

The factor Cs of the measured data which is made variable depending on a ratio of $r/\Delta x$ (r is a radius of the detecting aperture, and $\Delta x$ the averaged diameter of the speckles) becomes about one when the ratio of $r/\Delta x$ is zero, i.e., pointed detection is established, and decreases with the increasing $r/\Delta x$ as shown in FIG. 15. The rate of decrease is slow in the range of $r/\Delta x \lesssim 1$ and rapid in the range of $r/\Delta x \gtrsim 1$, then tending to be constant. This is proportional to $(r/\Delta x)^2$.

The factor $<n>$ directly proportional to the detected amount of light increases proportionally to $(r/\Delta x)^2$. Thus, the fluctuation rate Rf remarkably decreases in the range of $r/\Delta x \lesssim 1$ and slowly decreases in the range of $r/\Delta x \gtrsim 1$, becoming to be constant. This is because the decrease of Cs is canceled by the increase of $<n>$. This means that the greater $r/\Delta x$ than necessary is meaningless.

On the other hand, the too great $r/\Delta x$ makes the correlation time $\tau c$ long with the result of poor response. From FIG. 15 it will be understood that the setting of the aperture radius in the range $1 \lesssim r/\Delta x \lesssim 5$ after which the fluctuation rate becomes constant guarantees the extraction of correlation data with sufficient convergence. The characteristics as shown in FIG. 15 have been found to be typical for scattering objects such as living body, fluid, frosted glass, etc., which scatters light to produce speckles.

The measured data with a great fluctuation are preferably removed because they produce a big error. Thus, the microcomputer automatically calculates the fluctuation rate Rf for the measured data according to the formula (5) to determine the fluctuation of data quantitatively. The variables Cs, $<n>$, T and $\Delta t$ are easily obtained based on parameters set in the correlator 53 or on the measured data. A reference value Rfr is provided to make comparison with the calculated fluctuation rate and to provide an employment criterion, i.e., employed if Rf<Rfr and not employed if Rf>Rfr.

The rate of fluctuation is calculated by the above formula (5). The above described reference value of the fluctuation rate may be 10 to 20%.

In the above embodiment, instead of the minute circular detecting aperture, an optical fiber with its entrance made open may be employed. In this case, the core diameter is taken as aperture diameter, so that the invention will also be applicable to such a variation.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological diagnosis apparatus comprising:
    means for projecting a laser beam of prescribed diameter at a region of an eye fundus to produce a laser speckle pattern formed by light scattered from tissues of the eye fundus;
    detecting means including a minute circular detecting aperture for photoelectrically detecting movement of the laser speckle pattern as fluctuation in a light intensity of speckles at an observation plane;
    processing means for processing the intensity fluctuation of the speckle pattern by calculating photon correlation function data therefrom to determine the blood flow state in the eye fundus tissue;
    evaluating means for evaluating a rate of fluctuation of the photon correlation function data; and
    determining means for determining a radius of the detecting aperture dependent on the rate of fluctuation of the photon correlation function data.

2. An ophthalmological diagnosis apparatus according to claim 1, wherein the determining means includes means to determine the radius of the detecting aperture to be one to five times as great as the averaged diameter of speckles which constitute the speckle pattern.

3. An ophthalmological diagnosis apparatus according to claim 1, wherein the evaluating means includes means for calculating the rate of fluctuation (Rf) determined by a formula, $$Rf = 100/(Cs<n>(T/\Delta t)^{\frac{1}{2}}) \ (\%)$$

where Cs is a ratio of a maximum of correlation value with a base line subtracted therefrom to the base line and $<n>$ is the counted pulse value per unit sampling time $\Delta t$ which is averaged over a period of time T.

4. An ophthalmological diagnosis apparatus according to claim 1, wherein the evaluating means includes means to determine that the photon correlation function data are invalid when a convergence rate thereof is below a predetermined value.

5. An ophthalmological diagnosis apparatus, comprising: projecting means for projecting a laser beam at a region of an eye fundus to produce a laser speckle pattern from tissues of the eye fundus; detecting means including a detecting aperture for photoelectrically detecting movement of the laser speckle pattern as a light intensity fluctuation of the laser speckle pattern and generating an intensity signal in response thereto; calculating means receptive of the intensity signal for calculating correlation function data in response thereto to determine the blood flow state in the eye fundus tissue and produce a speckle signal dependent on the correlation function data; evaluating means receptive of the speckle signal for evaluating a rate of fluctuation of the correlation function data, said rate of fluctuation being calculated by a formula, $Rf = 100/(Cs<n>(T/\Delta t)^{\frac{1}{2}}) \ (\%)$ where Cs is a ratio of maximum correlation value with a base line subtracted therefrom to the base line and $<n>$ is a counted pulse value per unit sampling time $\Delta t$ which is averaged over a period of time T; and determining means for determining a radius of the detecting aperture dependent on the rate of fluctuation.

6. An ophthalmological diagnosis apparatus according to claim 5, wherein the determining means includes means to determine the radius of the detecting aperture to be one to five times as great as an averaged diameter of speckles which constitute the speckle pattern.

7. An ophthalmological diagnosis apparatus according to claim 5, wherein the evaluating means includes means to determine that the correlation function data are invalid when a convergence rate thereof is below a predetermined value.

* * * * *